(12) United States Patent
Farzin-Nia et al.

(10) Patent No.: US 6,267,589 B1
(45) Date of Patent: Jul. 31, 2001

(54) ORTHODONTIC SCREW EXPANSION DEVICE

(75) Inventors: Farrokh Farzin-Nia, Inglewood; Craig Andreiko, Alta Loma, both of CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 09/444,329

(22) Filed: Nov. 19, 1999

Related U.S. Application Data

(63) Continuation of application No. 09/076,969, filed on May 13, 1998, now abandoned.

(51) Int. Cl.[7] .................................................. A61C 3/00
(52) U.S. Cl. ................................................................ 433/7
(58) Field of Search ...................................................... 433/7

(56) References Cited

U.S. PATENT DOCUMENTS

| | | |
|---|---|---|
| 597,582 | 1/1898 | Knapp ........................ 433/7 |
| 934,958 | 9/1909 | Case .......................... 433/7 |
| 3,832,778 | 9/1974 | Wallshein ................... 433/7 |
| 3,921,294 | 11/1975 | Wallshein ................... 433/7 |
| 4,144,643 | 3/1979 | Krygier ...................... 433/7 |
| 4,347,054 | 8/1982 | Kraus et al. ............... 433/7 |
| 4,348,179 | 9/1982 | Nardella .................... 433/7 |
| 5,002,485 | 3/1991 | Aagesen ..................... 433/7 |
| 5,281,133 | 1/1994 | Farzin-Nia ................. 433/7 |
| 5,564,920 | 10/1996 | Klapper et al. ............ 433/7 |

*Primary Examiner*—John J. Wilson
(74) *Attorney, Agent, or Firm*—Wood, Herron & Evans L.L.P.

(57) ABSTRACT

An orthodontic expansion device which may be used for expanding the palate of a patient or for other orthodontic treatments. The expansion device is a compact design which essentially uses tubular-shaped screw actuating structure and rod-shaped screw actuating structure for connecting first and second legs which are respectively attached to a patient's teeth. When at least one of the screw actuating structures is rotated, expansion of the legs may be effected during the treatment of a patient. The legs may be connected rigidly to the screw actuating structure or may form part of the screw actuating structure.

11 Claims, 2 Drawing Sheets

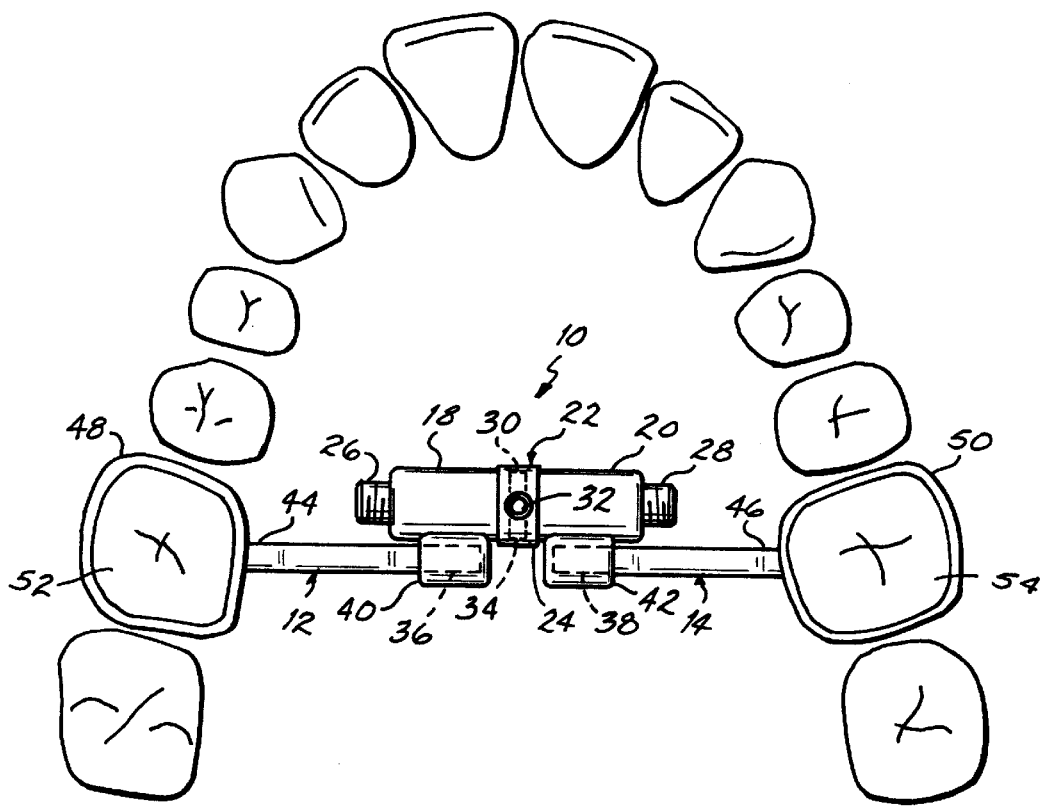
FIG. I
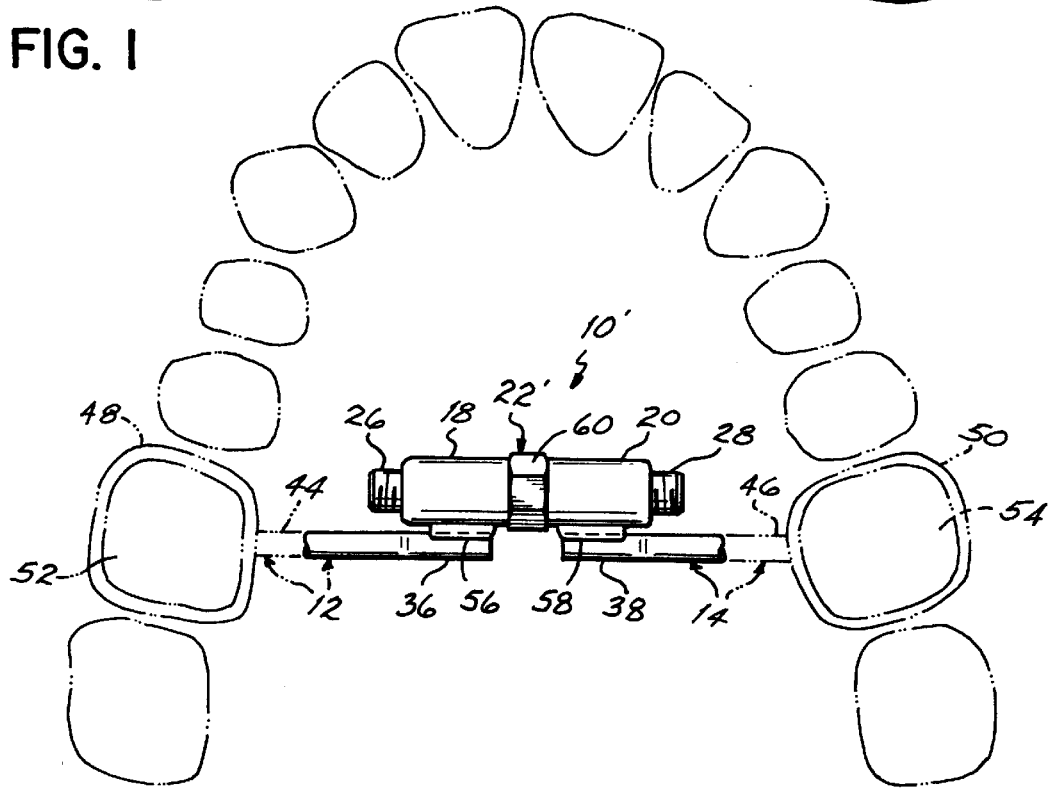
FIG. IA

ORTHODONTIC SCREW EXPANSION DEVICE

This application is a continuation of application Ser. No. 09/076,969 filed May 13, 1998 (now, abandoned), the disclosure of which is fully incorporated herein by reference.

FIELD OF THE INVENTION

The present invention relates to orthodontic expansion devices in general and, more specifically, to those devices that utilize screw actuators to effect the expansion.

BACKGROUND OF THE INVENTION

Screw expansion devices are well known in the orthodontic field to correct various dental abnormalities or occlusions. One of several types of orthodontic problems addressed by the present invention relates to an arch width or palate that is too narrow. This problem can also cause various other medical and dental difficulties. One general type of expansion device, commonly referred to as a rapid palatal expansion (RPE) device, includes a support apparatus having a screw mechanism. The support apparatus and screw mechanism are typically affixed to legs rigidly connected to teeth on opposite sides of the patient's maxillary jaw. As the screw mechanism is rotated, an expansive force may be applied to the palate. Successive expansions over time deliver the necessary forces for widening the palate. These devices are often used on narrow palates of children while the jaw and other dental structure are in formative stages For example, since the palate typically contains cartilage between the plates at earlier growth stages, palatal expanders are often a recommended course of treatment. It follows that the space available in the mouth of a child is relatively small and, therefore, size considerations and comfort issues become even more important in these cases.

Known orthopedic screw expansion devices are disclosed in U.S. Pat. Nos. 4,347,054; 5,002,485; and 5,281,133. As exemplified by these patents, expanders currently in commercial production include a screw unit for activation, four legs that are connected to molars and bicuspids of the patient and a supporting structure for maintaining structural integrity of the device. As also shown in these patents, the supporting structure of such typical devices may take up significant space within the mouth of a patient. Also, due to the size of the support structure, these devices cannot be situated at the uppermost arch region and cannot easily be used for mandibular expansion. U.S. Pat. No. 5,564,920 illustrates a palatal expander having a somewhat lower profile, however, the device is otherwise too complicated.

Another disadvantage of currently available orthodontic expanders is that the support structure can block the holes used for accepting a tool when actuating or turning the screw expander. Also, current expanders are typically substituted with a transpalatal arch after the expansion is complete to give the patient a more comfortable stabilizer at this stage of the treatment. Therefore, it has become apparent that improvements would be desirable in this general field to improve patient comfort and decrease any constraints on the use of such devices caused, for example, by the space consuming support structure. It would also be desirable to specifically reduce or even eliminate the need for substituting a palatal expander with a transpalatal arch.

SUMMARY OF THE INVENTION

The present invention therefore provides significant improvements in patient comfort by exhibiting a low profile and allowing installation closer to the patient's palate. In particular, the expansion device of the present invention eliminates the bulky supports in past devices and therefore eliminates problems associated with those supports. The expansion device of this invention may also be used more readily for various orthodontic applications, such as palatal expansion or mandibular expansion, due to the lower profile of the device. Further advantages of the invention include the elimination or reduction in the need to replace the expansion device with a transpalatal arch after a palatal expansion and other improvements related to the streamlined design and reduction in costs typically associated with such devices.

In fulfillment of these and other advantages and objectives of the invention, one general type of orthodontic expansion device of this invention includes tubular-shaped screw actuating structure having respective oppositely threaded internal thread portions. The invention also generally includes first and second legs each having inner and outer ends with the outer ends being adapted for attachment to a patient's teeth. Finally, in devices constructed in accordance with this embodiment of the invention, rod-shaped screw actuating structure is provided having respective oppositely threaded external thread portions in engagement with the internal thread portions of the tubular-shaped screw actuating structure. The tubular-shaped screw actuating structure and rod-shaped screw actuating structure cooperate to further connect the inner ends of the respective first and second legs such that rotation of at least one of the screw actuating structures moves the first and second legs toward or away from each other. In a more specific embodiment, the tubular-shaped screw actuating structure can comprise first and second tubular members each having one of the internal thread portions. In another similarly operating embodiment, the tubular-shaped screw actuating structure is a single piece structure and the oppositely threaded internal thread portions are threaded bores located at opposite ends of the single piece tubular-shaped structure.

When first and second threaded tubular members are used in the invention, the rod-shaped screw actuating structure may be a rod having a central tool engagement portion and having the external thread portions on opposite ends thereof in engagement with the respective internal thread portions of the first and second tubular members. On the other hand, when the tubular-shaped screw actuating structure is a single piece structure, the inner ends of the first and second legs can include the rod-shaped screw actuating structure. In each case, when the tool engagement portion is rotated through the use of an appropriate tool, such as with a piece of wire or a wrench, the two legs will move toward or away from each other.

As another manner of describing the invention, an embodiment of the orthodontic expansion device may comprise a screw element including first and second oppositely threaded end portions and a tool engagement portion disposed between the end portions. First and second legs extend in opposite directions from the screw element and each leg includes an inner end which is threaded and an outer end which is adapted for attachment to the teeth of a patient. The threaded inner ends of the legs are respectively engaged with the threaded end portions of the screw element such that rotation of the screw element in one direction will move the first and second legs away from each other while rotation of the screw element in an opposite direction will move the first and second legs toward each other.

As mentioned above, the threaded portions on the inner ends of the legs may be external threads or, in accordance with this embodiment, the threaded inner ends of the legs may be internal threads. In the latter case, the first and second oppositely threaded end portions on the screw element are external threads.

Additional advantages and objectives of the invention will become more apparent to those of ordinary skill upon review the following detailed description of the preferred embodiments taken in conjunction with the drawings.

BRIEF DESCRIPTION OF THE DRAWINGS

FIG. 1 is a bottom plan view illustrating one embodiment of the orthodontic expansion device of the present invention positioned between the maxillary teeth of a patient;

FIG. 1A is a bottom plan view similar to FIG. 1 but showing a modified embodiment of the orthodontic expansion device;

DETAILED DESCRIPTION OF THE PREFERRED EMBODIMENTS

Figure 2:
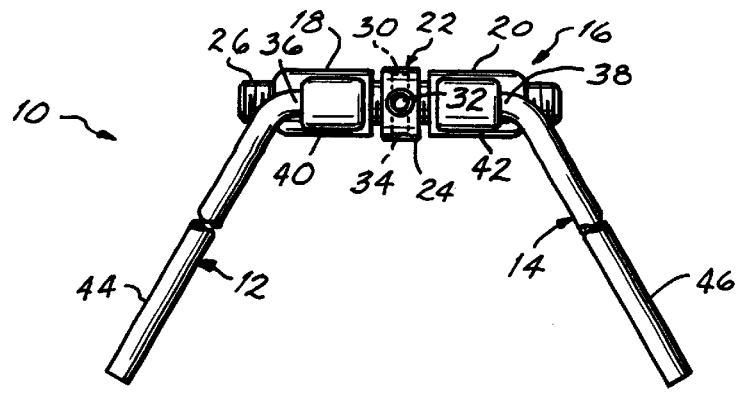
FIG. 2 is an elevational view of the orthodontic expansion device shown in FIG. 1, but shown detached from the patient's teeth and slightly expanded.

Referring first to FIGS. 1 and 2, a screw expansion device 10 constructed in accordance with one preferred embodiment of this invention includes a pair of rod-shaped legs 12, 14 which are connected together for expansion and retraction by screw actuating structure 16. In this embodiment, screw actuating structure 16 includes a pair of internally and oppositely threaded tubular members 18, 20. An externally threaded actuating element 22 includes a central tool engagement portion 24 and a pair of externally threaded portions 26, 28. Threaded portions 26, 28 are also oppositely threaded and respectively engaged within threaded tubular members 18, 20. Tool engagement portion 24 may include a plurality of bores 30, 32, 34 fully exposed for engagement by a suitable tool, such as a wire-type tool. Respective inner ends 36, 38 of legs 12, 14 are rigidly secured to tubular members 18, 20 by way of mounting members 40, 42. For example, inner ends 36, 38 may be brazed, soldered or welded within mounting members 40, 42 and brazing, soldering or welding may be used between mounting members 40, 42 and tubular members 18, 20. Outer ends 44, 46 of legs 12, 14 may be attached rigidly to bands 48, 50 also by methods such as brazing. These bands 48, 50 may then be epoxied or otherwise securely affixed to teeth, such as upper molars 52, 54 of a patient. The materials of construction for all the components used for the invention may be conventional stainless steels used for orthodontic purposes.

FIG. 1A illustrates one alternative construction to the embodiment shown in FIGS. 1 and 2. In the illustration of device 10', prime marks are used to denote that some elements are modified from the corresponding elements shown in FIGS. 1 and 2. The modifications are that inner ends 36, 38 of legs 12, 14 are directly affixed to the outer surfaces of the tubular members 18, 20, such as by welding 56, 58, and that an alternative hex-shaped tool engagement portion 60 is provided in substitution for tool engagement portion 24. It will be appreciated that each of the embodiments of FIGS. 1 and 1A operates in the same manner. That is, rotation of tool engagement portion 24 or 60 in one direction will cause tubular members 18, 20 and the attached legs 12, 14 to expand away from each other, as shown in FIG. 2, while rotation of tool engagement portion 24 or 60 in the opposite direction will have the opposite retractive effect on legs 12, 14.

Figure 3:
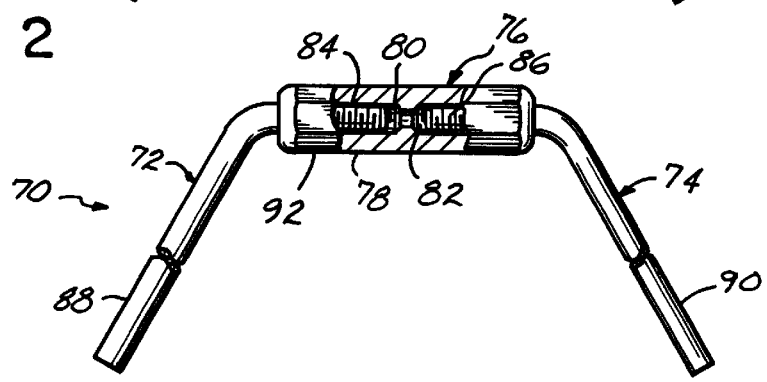
FIG. 3 is an elevational view similar to FIG. 2, but illustrating another alternative embodiment of the invention.
Figure 4:
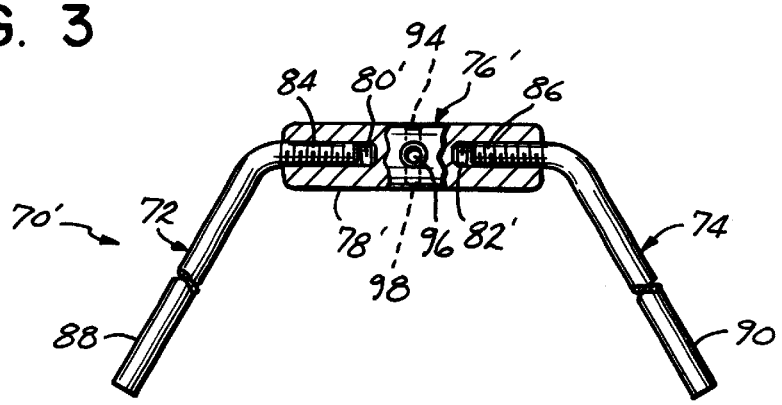
FIG. 4 is an elevational view of an expansion device similar to that shown in FIG. 3, but having a modified tool engagement structure.

FIGS. 3 and 4 illustrate expansion devices 70 and 70' which also use tubular, internally threaded actuating structure and externally threaded rod-shaped structure, but which differ in other regards with respect to the embodiments shown in FIGS. 1 and 1A. In this regard, FIG. 3 illustrates an expansion device 70 including a pair of legs 72, 74 that serve the same function as legs 12, 14. Screw actuating structure 76, including a single piece tubular-shaped member 78, is provided as an actuating element for moving legs 72, 74. Tubular member 78 includes oppositely threaded bores 80, 82 at respective ends thereof. The rod-shaped screw actuating structure takes the form of externally threaded inner ends 84, 86 of legs 72, 74. Legs 72, 74 have outer ends 88, 90 which may be bent, cut and suitable affixed to a patient's teeth as described with respect to the previous embodiments. In the embodiment shown in FIG. 3, the tool engagement portion of tubular-shaped member 78 comprises a hex-shaped surface 92.

In the embodiment shown in FIG. 4, prime marks are again used on elements in FIG. 4 that are somewhat modified from the corresponding elements shown in FIG. 3. The main difference between FIGS. 3 and 4 is that expansion device 70' includes a plurality of bores 94, 96, 98 as its tool engagement portion in place of the hex-shaped outer surface 92. It will further be appreciated that upon rotation of tubular-shaped member 78 or 78' in one direction, legs 72, 74 will move away from each other while rotation in the opposite direction will cause legs 72, 74 to have an opposite retractive movement. The term tubular-shaped member is used to broadly describe both elements 78 and 78'. However, within the meaning of this term, internally threaded bores 80, 82, 80', 82' may or may not communicate with one another.

Figure 5:
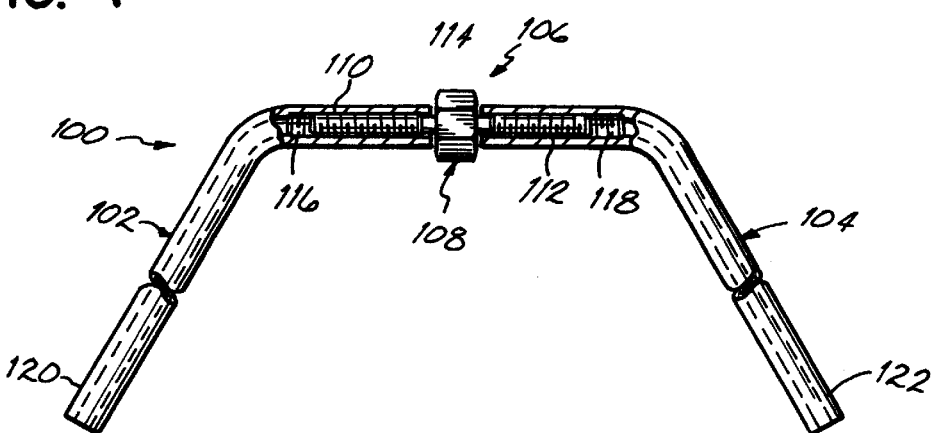
FIG. 5 is an elevational view similar to FIGS. 2–4, but illustrating another embodiment of the invention.

FIG. 5 illustrates yet another embodiment of an expansion device 100 constructed in accordance with the invention. Expansion device 100 more specifically includes a pair of legs 102, 104 which may serve the same functions as legs 12, 14 or 72, 74 of the previous embodiments. A screw actuating structure 106 is provided and includes a rod-shaped element 108 comprising oppositely threaded, external thread portions 110, 112 connected by a central tool engagement portion 114. Inner ends of legs 102, 104 include respective oppositely threaded internal thread portions 116, 118 which receive external threaded portions 110, 112. Legs 102, 104 have outer ends 120, 122 which may be bent, cut and suitably affixed to a patient's teeth as previously described. It will be appreciated that when tool engagement portion 114 is rotated in one direction, legs 102, 104 will expand away from each other while rotation of tool engagement portion 114 in the opposite direction will cause legs 102, 104 to have an opposite retractive movement.

While the present invention has been illustrated by a description of the preferred embodiments and while these embodiments have been described in considerable detail, it is not the intention of the Applicant to restrict or in any way limit the scope of the appended claims to such detail. Additional advantages and modifications will readily appear to those skilled in the art. These modifications can include various combination of the separate features described herein. The invention in its broader aspects is therefore not limited to the specific details, representative apparatus and methods as shown and described, but should only be defined by the appended claims.

What is claimed is:

1. A low profile orthodontic expansion device alternatively useful in both palatal and mandibular expansion procedures, the device comprising:

first and second tubular-shaped screw actuating structures having respective right and left hand internal thread portions, teeth attachment structure consisting of first and second legs each having inner and outer ends with the outer ends being adapted for attachment to a patient's teeth and the inner ends rigidly affixed to said respective first and second tubular-shaped screw actuating structures, and rod-shaped screw actuating structure consisting of a pair of oppositely threaded, first and second external thread portions separated by a tool engagement portion configured to allow rotation of said rod shaped screw actuating structure by a tool, said first and second external thread portions engaged with the internal thread portions of the respective first and second tubular-shaped screw actuating structures, wherein said rod-shaped screw actuating structure is formed as a single piece component and the first and second tubular-shaped screw actuating structures and the rod-shaped screw actuating structure cooperate to further connect the inner ends of the first and second legs such that the first and second legs and the screw actuating structure together form an arch shape to alternatively conform to the palatal arch of the patient's mouth and to the mandibular region of the patient's mouth, and rotation of said tool engagement portion rotates said first and second external thread portions to expand the first and second legs away from each other.

2. The orthodontic expansion device of claim 1, wherein the tubular-shaped screw actuating structure includes first and second tubular members each having one of the internal thread portions.

3. The orthodontic expansion device of claim 1, wherein the tool engagement portion includes a plurality of tool receiving bores in an external surface of the tubular-shaped screw actuating structure.

4. The orthodontic expansion device of claim 1, wherein the tool engagement portion includes a hex-shaped outer surface.

5. A low profile orthodontic expansion device alternatively useful in both palatal and mandibular expansion procedures, the device comprising:

teeth attachment structure consisting of first and second legs having active inner and outer ends, the inner ends of the legs being externally threaded opposite directions and the outer ends of the legs being adapted for attachment to a patient's teeth, and a screw element consisting of internally threaded first and second end portions and a tool engagement portion, wherein the internally threaded first and second end portions are respectively engaged with the externally threaded inner ends of said legs such that the first and second legs and the screw element together form an arch shape to conform alternatively to the palatal arch of the patient's mouth and to the mandibular region of the patient's mouth, and rotation of the tool engagement portion of said screw element in one direction will move the first and second legs away from each other and rotation of the screw element in an opposite direction will move the first and second legs toward each other.

6. The orthodontic expansion device of claim 5, wherein the tool engagement portion includes a plurality of bores for receiving a tool.

7. The orthodontic expansion device of claim 5, wherein the tool engagement portion includes a hex-shaped outer surface for receiving a tool.

8. The orthodontic expansion device of claim 5, wherein a band is connected to the outer end of each leg for encircling a tooth on each side of the patient's mouth.

9. A low profile orthodontic expansion device alternatively useful in both palatal and mandibular expansion procedures, the device comprising:

a screw element consisting of first and second end portions threaded externally in opposite directions, and a tool engagement portion disposed between the end portions, and teeth attachment structure consisting of first and second legs extending in opposite directions from the screw element and each leg having an inner end and an outer end, the inner ends of the legs being respectively internally threaded and respectively engaged with the first and second externally threaded end portions of the screw element such that the first and second legs and the screw element together form an arch shape to alternatively conform to the palatal arch of the patient's mouth and to the mandibular region of the patient's mouth, and the outer ends being adapted for attachment to teeth of a patient, wherein rotation of the tool engagement portion of said screw element in one direction will move the first and second legs away from each other and rotation of the tool engagement portion of said screw element in an opposite direction will move the first and second legs toward each other.

10. The orthodontic expansion device of claim 9, wherein the tool engagement portion includes a plurality of tool receiving bores.

11. The orthodontic expansion device of claim 9, wherein the tool engagement portion includes a hex-shaped outer surface.

* * * * *

UNITED STATES PATENT AND TRADEMARK OFFICE
CERTIFICATE OF CORRECTION

PATENT NO. : 6,267,589 B1
DATED : July 31, 2001
INVENTOR(S) : Farzin-Nia et al.

It is certified that error appears in the above-identified patent and that said Letters Patent is hereby corrected as shown below:

Column 5,
Line 53, reads "legs having active inner and outer ends, the inner ends of the legs being externally threaded opposite directions" and should read -- legs having respective inner and outer ends, the inner ends of the legs being externally threaded in opposite directions --.

Signed and Sealed this

Eleventh Day of June, 2002

Attest:

Attesting Officer

JAMES E. ROGAN
*Director of the United States Patent and Trademark Office*